(12) United States Patent
Johnson

(10) Patent No.: US 10,688,208 B2
(45) Date of Patent: Jun. 23, 2020

(54) SYSTEMS AND METHODS FOR DECONTAMINATION AND/OR SANITIZATION

(71) Applicant: Qlean Tech IP, LLC, Mendota Heights, MN (US)

(72) Inventor: Thomas Johnson, Mendota Heights, MN (US)

(73) Assignee: Qlean Tech IP, LLC, Mendota Heights, MN (US)

( * ) Notice: Subject to any disclaimer, the term of this patent is extended or adjusted under 35 U.S.C. 154(b) by 0 days.

(21) Appl. No.: 16/057,146

(22) Filed: Aug. 7, 2018

(65) Prior Publication Data
US 2019/0030197 A1 Jan. 31, 2019

Related U.S. Application Data

(62) Division of application No. 15/646,694, filed on Jul. 11, 2017, now Pat. No. 10,086,098.

(Continued)

(51) Int. Cl.
*A61L 2/18* (2006.01)
*B08B 3/12* (2006.01)
(Continued)

(52) U.S. Cl.
CPC .............. *A61L 2/18* (2013.01); *A61L 2/0011* (2013.01); *A61L 2/0047* (2013.01); *A61L 2/0088* (2013.01); *A61L 2/035* (2013.01); *A61L 2/10* (2013.01); *A61L 2/22* (2013.01); *A61L 2/24* (2013.01); *B01F 3/0865* (2013.01); *B01F 5/0413* (2013.01); *B08B 1/006* (2013.01); *B08B 3/12* (2013.01); *B08B 7/0057* (2013.01);
(Continued)

(58) Field of Classification Search
None
See application file for complete search history.

(56) References Cited

U.S. PATENT DOCUMENTS 4,710,233 A 12/1987 Hohmann et al.
5,445,722 A 8/1995 Yamaguti et al.
(Continued)

FOREIGN PATENT DOCUMENTS

WO WO-2017058772 A1 4/2017

OTHER PUBLICATIONS

"", Second International Symposium: Electrochemical Activation in Medicine, Agriculture and Industry(Summaries of Papers and Brief Reports), Copyright © RSCECAT Int., Ltd., Technologytransfer Center, (1999), 491 pgs.

(Continued)

*Primary Examiner* — Eric W Golightly
(74) *Attorney, Agent, or Firm* — Schwegman Lundberg & Woessner, P.A.

(57) ABSTRACT

Generally discussed herein are systems, apparatuses, and methods for decontamination and/or sanitization. A method of decontamination or sanitization can include providing, by a water inlet, water, mixing fluids, at an adapter coupled to a catholyte tank, an anolyte tank, and the water inlet, including two or more of (1) catholyte from a catholyte tank, (2) the provided water from the water inlet, and (3) anolyte from an anolyte tank, providing, by an outlet coupled to the adapter, the mixed fluid, and irradiating, by an ultraviolet source, a portion of a user between a decontamination process and a sanitization process.

19 Claims, 5 Drawing Sheets

Related U.S. Application Data

(60) Provisional application No. 62/515,190, filed on Jun. 5, 2017, provisional application No. 62/456,907, filed on Feb. 9, 2017.

(51) Int. Cl.

| | | |
|---|---|---|
| *B08B 7/00* | (2006.01) | |
| *B08B 1/00* | (2006.01) | |
| *C02F 1/461* | (2006.01) | |
| *B01F 3/08* | (2006.01) | |
| *B01F 5/04* | (2006.01) | |
| *C02F 1/467* | (2006.01) | |
| *A61L 2/00* | (2006.01) | |
| *A61L 2/24* | (2006.01) | |
| *A61L 2/03* | (2006.01) | |
| *A61L 2/10* | (2006.01) | |
| *A61L 2/22* | (2006.01) | |
| *C02F 103/02* | (2006.01) | |
| *C02F 1/32* | (2006.01) | |

(52) U.S. Cl.
CPC .......... *C02F 1/4618* (2013.01); *C02F 1/4674* (2013.01); *A61L 2202/11* (2013.01); *A61L 2202/14* (2013.01); *A61L 2202/17* (2013.01); *C02F 1/32* (2013.01); *C02F 2103/02* (2013.01); *C02F 2209/06* (2013.01); *C02F 2209/44* (2013.01)

(56) References Cited

U.S. PATENT DOCUMENTS

| | | | |
|---|---|---|---|
| 5,759,489 A | 6/1998 | Miura et al. | |
| 6,022,512 A | 2/2000 | Tanaka et al. | |
| 6,059,941 A | 5/2000 | Bryson et al. | |
| 6,274,009 B1 | 8/2001 | Krafton et al. | |
| 6,379,632 B1 | 4/2002 | Kinoshita et al. | |
| 6,632,973 B1 | 10/2003 | Miyake et al. | |
| 6,770,150 B1 | 8/2004 | Duckett et al. | |
| 8,282,974 B2 | 10/2012 | Johnson et al. | |
| 9,981,054 B2 | 5/2018 | Johnson et al. | |
| 10,086,098 B2 | 10/2018 | Johnson | |
| 2004/0007255 A1 | 1/2004 | Labib et al. | |
| 2004/0156744 A9 | 8/2004 | Stanley | |
| 2007/0214815 A1 | 9/2007 | Lewkowitz et al. | |
| 2009/0236235 A1 | 9/2009 | Wilkins et al. | |
| 2010/0252074 A1 | 10/2010 | Sewake et al. | |
| 2014/0013580 A1 | 1/2014 | Limback et al. | |
| 2015/0246316 A1 | 9/2015 | Chancellor | |
| 2017/0255209 A1 | 9/2017 | Johnson | |
| 2018/0221524 A1 | 8/2018 | Johnson | |

OTHER PUBLICATIONS

"U.S. Appl. No. 15/581,451, Notice of Allowance dated Jan. 4, 2018", 11 pgs.

"U.S. Appl. No. 15/581,451, Preliminary Amendment filed May 24, 2017", 7 pgs.

"U.S. Appl. No. 15/581,451, Response filed Nov. 21, 2017 to Restriction Requirement dated Sep. 29, 2017", 9 pgs.

"U.S. Appl. No. 15/581,451, Restriction Requirement dated Sep. 27, 2017", 8 pgs.

"U.S. Appl. No. 15/646,694, Non Final Office Action dated Dec. 28, 2017", 17 pgs.

"U.S. Appl. No. 15/646,694, Notice of Allowance dated May 1, 2018", 9 pg.

"U.S. Appl. No. 15/646,694, PTO Response to Rule 312 Communication dated Aug. 29, 2018", 2 pgs.

"U.S. Appl. No. 15/646,694, Response filed Mar. 27, 2018 to Non Final Office Action dated Dec. 28, 2017", 13 pgs.

"U.S. Appl. No. 15/646,694, Response filed Nov. 21, 2017 to Restriction Requirement dated Sep. 26, 2017", 8 pgs.

"U.S. Appl. No. 15/646,694, Restriction Requirement dated Sep. 26, 2017", 7 pgs.

"Aquaox ECS Series", Aquaox Onsite Production of Electrolyzed Water, catalog/brochure, "To reduce chemicals and replace them with ecological friendly disinfectants", printed at least as early as Sep. 2, 2015., 1-6.

"International Application Serial No. PCT/US2016/053928, International Preliminary Report on Patentability dated Apr. 12, 2018", 13 pgs.

"International Application Serial No. PCT/US2016/053928, International Search Report dated Feb. 16, 2017", 4 pgs.

"International Application Serial No. PCT/US2016/053928, Invitation to Pay Add'l Fees and Partial Search Rpt Rcvd dated Nov. 28, 2016", 3 pgs.

"International Application Serial No. PCT/US2016/053928, Written Opinion dated Feb. 16, 2017", 11 pgs.

Swan, J.S., et al., "Elimination of biofilm and microbial contamination reservoirs in hospital washbasin U-bends by automated cleaning and disinfection with electrochemically activated solutions", Journal of Hospital Infection 94.2, (2016), 169-174.

Johnson, Thomas, "Evolved Sanitary Operations Platforms", Johnson Diversified Products, Inc., (2013), 46 pgs.

SYSTEMS AND METHODS FOR DECONTAMINATION AND/OR SANITIZATION

CLAIM FOR PRIORITY

This patent application is a divisional of and claims the benefit of priority to U.S. patent application Ser. No. 15/646,694, filed Jul. 11, 2017, and issued as U.S. Pat. No. 10,086,098 on Oct. 2, 2018, which is a non-provisional of and claims the benefit of priority, to U.S. Provisional Patent Application Ser. No. 62/515,190, filed Jun. 5, 2017, and U.S. Provisional Patent Application Ser. No. 62/456,907, filed. Feb. 9, 2017, which applications are incorporated herein by reference in their entirety.

TECHNICAL FIELD

Embodiments discussed herein relate to devices, systems, and methods for decontamination and/or sanitization, such as by using catholyte and anolyte, respectively.

BACKGROUND

Many entities use toxic chemicals for cleaning and sanitization of their facilities and/or equipment. These toxic chemicals can be detrimental to foodservice retailers as the toxic chemicals can get into the food or drinks that are served. In other industries, the patrons of the facilities may come in contact with the toxic chemicals.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various embodiments or examples discussed in the present document.

DETAILED DESCRIPTION

Embodiments in this disclosure generally relate to decontamination (e.g., cleaning) and/or sanitization.

Anolyte and catholyte can be used in place of these toxic chemicals previously discussed. Anolyte and catholyte are not only non-toxic and consumable, but can also be easily produced on-site at a facility that uses anolyte and catholyte. This makes anolyte and catholyte production and use a cost-effective solution for the sanitization and cleaning needs of a facility.

Figure 1:
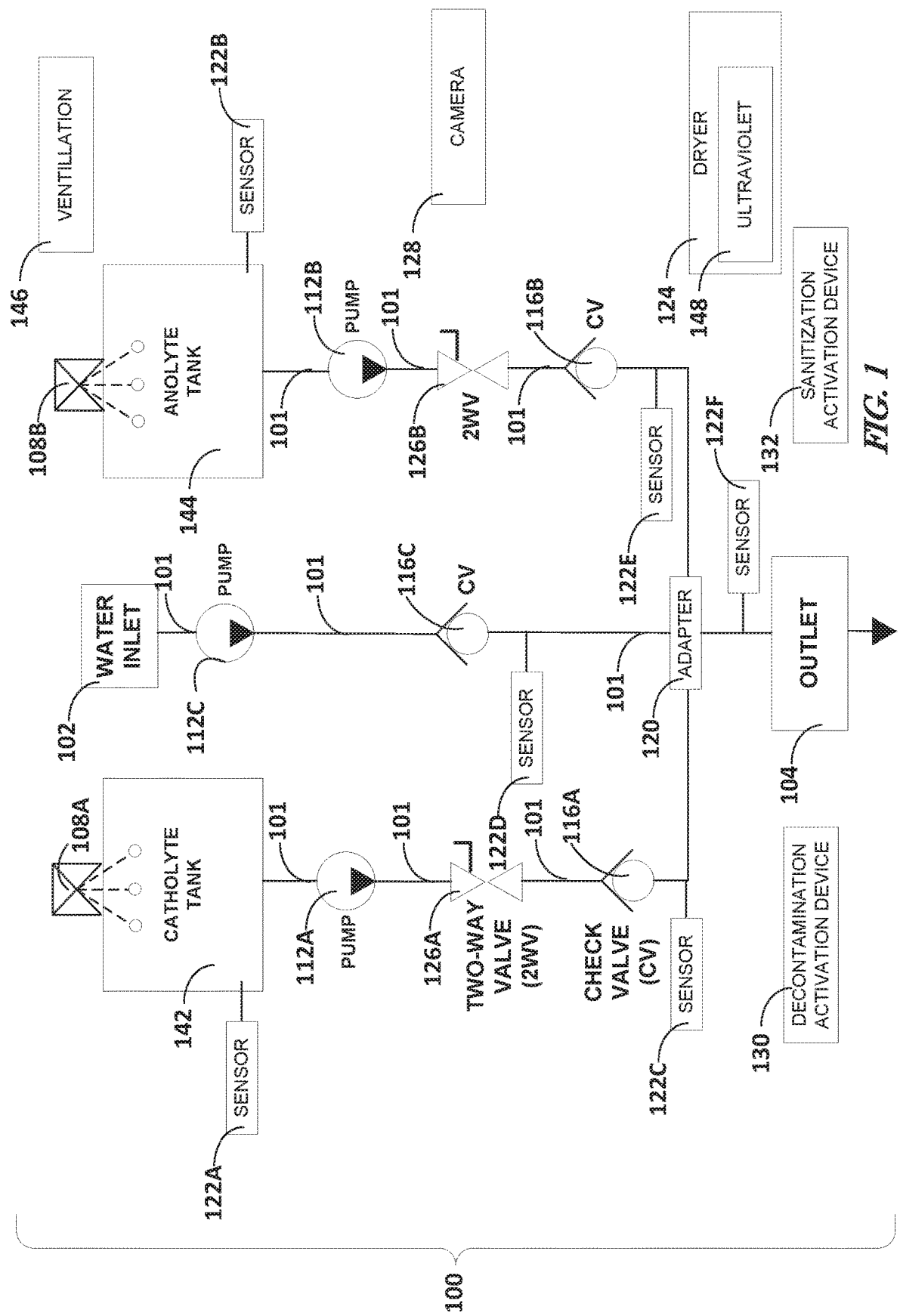
FIG. 1 illustrates, by way of example, a diagram of an embodiment of a portion of a system for performing a decontamination and/or sanitization process.

FIG. 1 illustrates, by way of example, a diagram of an embodiment of a system 100 for decontamination and/or sanitization. The system 100 as illustrated includes a conduit 101, a water inlet 102, a fluid outlet 104, a catholyte tank 142, and an anolyte tank 144. The water inlet 102 is optional. The system 100 as illustrated further includes a sensor 108A and 108B, a pump 112A, 112B, and 112C, a first valve 126A and 126B, and a second valve 116A and 116B. The sensor 108A and 08B, a pump 112A, 112B, and 112C, the valve 126A and 126B, and the check valve 116A and 116B are optional.

The conduit 101 may be a hollow, usually annular, length of material through which fluids may flow without leaking out of sidewalls of the conduit 101. The material of the conduit 101 may include a polymer, ceramic, metal, a combination thereof or other material. An inner diameter of the conduit 101 and a flow rate of the fluid in the conduit 101 may determine a volume of fluid that may be provided to the outlet 104.

The water inlet 102 provides potable water to the conduit 101. Potable water complies with 40 C.F.R. 121, the Safe Drinking Water Act and National Primary Drinking Water regulations. Treated water may be water with ≤1 grain of hardness (<17.1 parts per million (PPM) total dissolved solids (TDS)).

The water from the water inlet 102, in one or more embodiments may be reverse osmosis water. In one or more embodiments, the water from the water inlet 102 includes less than one part per million (ppm) of each of hardness, fluoride, iron, magnesium, and borax and borate. In one or more embodiments, a flow rate of the water from the water inlet 102 may be between about 22-30 gallons per hour. In one or more embodiments, the water from the water inlet may be at a pressure of about forty-five to fifty pounds per square inch (psi).

The pump 112C may be a variable displacement pump, dosing pump, or the like. A pump may be generally an electro-mechanical device using suction or pressure to move fluid(s). A dosing pump may be a displacement pump that provides a set flow rate of a fluid. The flow rate on a dosing pump may be fixed or variable. A variable displacement pump converts mechanical energy to fluid energy. The displacement, or amount of fluid provided by the variable displacement pump or dosing pump may be varied while the pump is running.

The valve 116C may be a one-way valve. A one-way valve allows fluid to flow from the inlet 102 and/or pump 112C to the adapter 120 and/or outlet 104. A one-way valve prevents fluid from flowing from the adapter and/or outlet 104 to the pump 112C and/or inlet 102. Other types of valves may be used in other embodiments.

The catholyte tank 142 holds a decontamination fluid, such as catholyte. Catholyte may be an electrolytically generated (activated) amphoteric surfactant(s). A precursor to catholyte can include salt dissolved in water. An oxidation reduction potential (ORP) of catholyte may be typically in a range of about negative two hundred millivolts to about negative one thousand one hundred millivolts. The salt(s) in the water may include sodium chloride (NaCl) to any other mineral salts in either a specific (e.g., 99.9% NaCl) or other proportion, as in ordinary drinking water.

The catholyte tank 142 as illustrated includes the sensor 108A. The sensor 122, in one or more embodiments may be a level sensor. A level sensor provides data indicative of a level of catholyte in the catholyte tank 142. The sensor 108A may include an ultrasonic sensor, capacitance sensor, hydrostatic pressure, or other level sensor. The sensor 108A may be submersible or dry.

The pump 112A may be similar to the pump 112C. The pump 112A may move catholyte from the catholyte tank 142 in the conduit 101. The pump 112A may provide the catholyte to the valve 126A. The valve 126A may be in fluid communication with fluid from the pump 112A and/or the catholyte tank 142. The valve 126A, when open, provides a path for catholyte to flow to the outlet 104. When closed, the valve 126A prevents catholyte from flowing to the outlet 104. The valve 126A may be opened or closed automatically, such as by an actuator, or manually. The valve 116A, in one or more embodiments, may be a two-way valve (2WV) or other type of valve.

The valve 116A may be a one-way valve that allows fluid flow in only one direction. The valve 116A may allow the catholyte from the catholyte tank 142 to flow therethrough to the outlet 104 and prevents fluid from flowing from the outlet 104 or adapter to the 2WV 126A, pump 112A, and/or catholyte tank 142.

The anolyte tank 144 holds a sanitization fluid, such as anolyte. Anolyte may be an electrolytically generated (activated) amphoteric surfactant(s). A precursor to catholyte can include salt dissolved in water. An oxidation reduction potential (ORP) of catholyte may be typically in a range of about negative two hundred millivolts to about negative one thousand one hundred millivolts. The salt(s) in the water may include sodium chloride (NaCl) to any other mineral salts in either a specific (e.g., 99.9% NaCl) or other proportion, as in ordinary drinking water. Anolyte may be an electrolytically generated (activated) amphoteric surfactant. Similar to catholyte, a precursor to anolyte includes brine (salt dissolved in water. The salt used may include sodium chloride (NaCl) or other mineral salt in generally any proportion. The ORP of anolyte may be typically in a range of about positive five hundred millivolts to about positive one thousand two hundred millivolts.

The anolyte tank 144 as illustrated includes a sensor 108B. The sensor 108B may be a level sensor. A level sensor provides data indicative of a level of anolyte in the anolyte tank 144. The sensor 108B may include an ultrasonic sensor, capacitance sensor, hydrostatic pressure, or other level sensor. The sensor 108B may be submersible or dry. The sensor 108B may be similar to the sensor 108A.

The pump 112B may be similar to the pump 112C. The pump 112B may move anolyte from the anolyte tank 144 in the conduit 101. The pump 112B may provide the anolyte to a valve 126B. The valve 126B may be in fluid communication with fluid from the pump 112B and/or the anolyte tank 144. The valve 126B, when open, provides a path for anolyte to flow to the outlet 104. When closed, the valve 126B prevents anolyte from flowing to the outlet 104. The valve 126B may be opened or closed automatically, such as by an actuator, or manually. The valve 126B, in one or more embodiments, may be a 2WV or other type of valve.

The valve 116B may be a one-way valve that allows fluid flow in only one direction. The valve 116B allows the anolyte from the anolyte tank 144 to flow therethrough to the outlet 104 and prevents fluid from flowing from the outlet 104 or adapter 120 to the valve 126B, pump 112B, and/or anolyte tank 144.

The catholyte and/or the anolyte may be provided through an electrolysis device. An electrolysis device takes dilute brine (saltwater) as input, applies an electrical current to the received brine, and produces concentrated anolyte and catholyte. Saltwater, anolyte, and catholyte are examples of electrolytes.

The adapter 120 may be a multiple input component with one or more outputs. The adapter 120 may provide a path through which catholyte from the catholyte tank 142 may be mixed with water from the water inlet 102 and/or anolyte from the anolyte tank 144. In one or more embodiments, a path of the adapter 120 through which the catholyte and water are mixed and a path of the adapter 120 through which the anolyte and water are mixed may be separate, such that catholyte and anolyte are not mixed in the adapter 120. In such embodiments, the adapter 120 includes four inputs (one for catholyte, one for anolyte, and two for water) and one or more outputs (one for catholyte and water mixture and one for anolyte and water mixture, or one for both the catholyte and water mixture and anolyte and water mixture). In one or more embodiments, the adapter 120 includes three input paths that combine and are provided in a single output.

The outlet 104 receives the catholyte, anolyte, and/or water, such as mixed. The outlet 104 may include a valve, such as may be automatically or manually controlled. The outlet 104 may include a structure similar to a faucet, for example. The outlet 104 may include one or more valves to control a heat of a fluid provided to the outlet 104. The outlet 104 may include one or more valves to control a volume of a fluid provided to the outlet 104. The outlet 104, in one or more embodiments, may be a hand hygiene sink, appliance, and/or appurtenance (HHSA). The outlet 104 may include an enclosed atmospherically controlled chamber that captures, contains, condenses, drains, and/or dries one or more aerosol(s) generated in a decontamination and/or sanitization process. Such an enclosure may help reduce risk(s) of contamination of a user, their attire, other surfaces, and/or other object or environment around the outlet 104. The outlet 104, in one or more embodiments, may be transparent. In one or more embodiments, the outlet 104 may include an ultrasonic nozzle, such as to help activate the catholyte and/or anolyte. The nozzle may provide bubbles, such as may provide kinetic energy that enhances the decontamination and/or sanitization.

In one or more embodiments, the outlet 104 may include one or more immersion baths (e.g., a catholyte immersion bath and/or an anolyte immersion bath) in which a user may submerge their hands or other part to be decontaminated and/or sanitized. The immersion bath(s) may include one or more ultrasonic transducers to produce sound that may be incident thereon. The ultrasonic transducers may enhance a decontamination and/or sanitization by the catholyte and/or anolyte immersion bath, respectively, such as by helping activate the catholyte and/or anolyte.

In embodiments that do not include one or more of the pumps 112A-C, the fluid mobilized by the respective pump 112A-C may be mobilized by a gravitational force or Venturi. In embodiments that use gravitational force, the catholyte tank 142, anolyte tank 144, and/or water inlet 102 may reside at an elevation that may be higher than the elevation of the outlet 104. The anolyte, catholyte, and/or water may be provided to the outlet 104, such as by opening a valve of the valve 126A-B and/or the outlet 104. In embodiments that use Venturi, the conduit 101 may include a venture tube. A Venturi tube includes one or more constrictions. A flow rate of a fluid in the region of the constriction increases relative to non-constricted regions, thus moving the fluid through the tube.

While the water inlet 102 is illustrated as including a single conduit connected thereto. The water inlet 102 may include a hot water conduit and a cold water conduit connected thereto. In such embodiments, the adapter 120 may include four inputs and a one or more outputs. One inlet for catholyte, one inlet for anolyte, one inlet for cold water, and one inlet for hot water. The outlet(s) of the adapter 120 may include a single outlet for combinations of hot water, cold water, catholyte and/or anolyte, or two outlets, one for combinations of hot water, anolyte, and/or catholyte, and a second outlet for combinations of cold water, anolyte, and/or catholyte.

The system 100 as illustrated includes optional sensor(s) 122A, 122B, 122C, 122D, 122E, and/or 122F, an optional dryer 124, and an optional camera 128. The sensor(s) 122 may include one or more of a flow sensor, free available chlorine sensor, pH sensor, conductivity sensor, or the like.

A flow sensor determines a volume of liquid displaced per unit time. Flow can be measured by determining a velocity of liquid over a known area or through a known volume. Alternatively, flow can be measured by determining forces produced by a flowing fluid as it overcomes a known constriction and inferring the flow rate based on the forces produced.

Free available chlorine may be generally expressed in PPM. Free available chlorine sensors may be placed in a flow stream or submersible. A free available chlorine sensor provides an indication of an amount of unbound chlorine in a fluid.

A pH sensor measures a concentration or activity level of hydrogen ions in an aqueous solution. The data from a pH sensor indicates how acidic or basic a solution is. pH means potential hydrogen and a measure of pH ranges from acid (a minimum pH of zero) to an alkaline base (a maximum pH of fourteen).

A conductivity sensor determines conductivity of an aqueous solution. The conductivity can be useful for determining a concentration of dissolved chemicals, such as the concentration of salt in a fluid. Conductivity is a measure of a solution's ability to carry an electric current. Conductivity is the reciprocal of the resistance of a solution.

The camera 128 may capture images, audio, and/or video of an area that includes the outlet 104 and a user of the outlet 104. The field of view of the camera 128 may include one or more hands, arms, face, or other body part of the user.

The dryer 124 provides a user an ability to dry a portion of their body. For example, the user may decontaminate their hand, arm, or other body part by placing it in a stream of fluid from the outlet 104, dry their body part using the dryer 124, sanitize their body part by placing it in another stream of fluid from the outlet 104, and dry their body part again using the dryer 124. The dryer 124 may include a towel, a napkin, an air blowing device, or the like. An optional ultraviolet (UV) source 148 may be integrated with the dryer 124, situated near the dryer 124, and/or separate from the dryer 124.

The system 100, in one or more embodiments, may include an optional decontamination activation device 130 and/or an optional sanitization activation device 132. The decontamination activation device 130 and/or sanitization activation device 132 may include a button, touch screen, proximity sensor, motion sensor, microphone, speaker, or the like. The decontamination activation device 130, when activated, provides an indication that a decontamination process is to begin. Similarly, the sanitization activation device 132, when activated, provides an indication that a sanitization process is to begin.

The system 100 as illustrated includes an optional ventilation 146. In one or more embodiments, the ventilation 146 may be coupled to the outlet 104, such as to remove aerosols, organisms removed using the decontamination or sanitization process, or other byproducts from the decontamination or sanitization process. The ventilation 146 includes a vacuum, carbon or other filter, fan, conduit, or other ventilation device. In one or more embodiments, the ventilation 146 may include a high efficiency particulate air (HEPA) filter.

The system 100 as illustrated includes an optional ultraviolet (UV) source 148. The UV source 148 may produce UVc radiation directed to the ventilation 146, and/or the outlet 104. The UV source 148 may kill organisms exposed to the radiation produced by the UV source 148.

Figure 2:
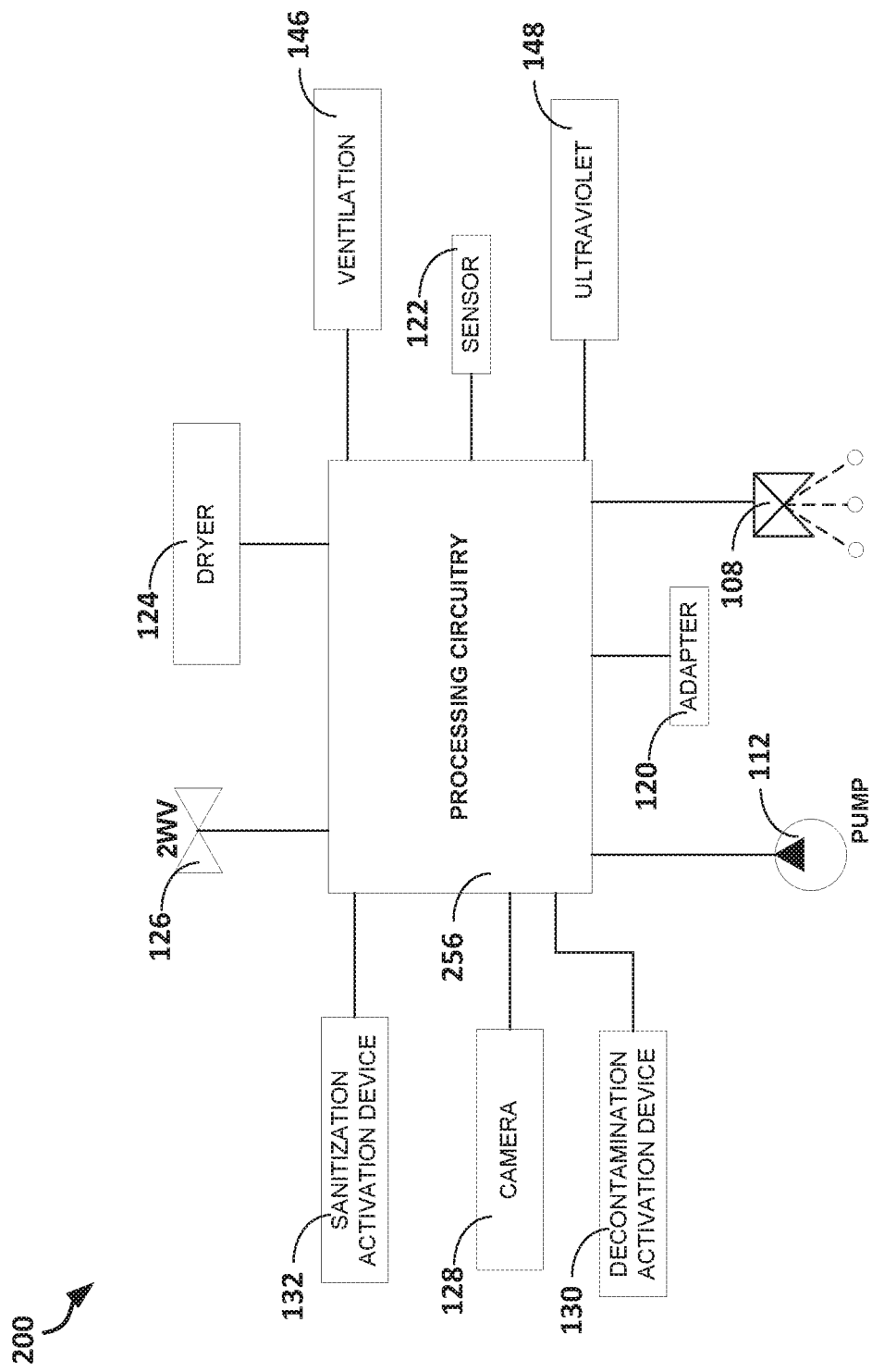
FIG. 2 illustrates, by way of example, a diagram of an embodiment of control circuitry to control one or more items of the system of FIGS. 1 and/or 3.

FIG. 2 illustrates, by way of example, a block diagram of an embodiment of a control system 200 to control items of the system 100. The control system 200 includes processing circuitry 256 electrically coupled, such as by a wired or wireless coupling or connection, to items of the system 100. The processing circuitry 256 includes a hardware processor or other components (e.g., transistor(s), resistor(s), capacitor(s), regulator(s), inductor(s), Boolean logic gate(s), clock(s), multiplexer(s), state logic, memory(s), diode(s), amplifier(s), modulator(s), demodulator(s), analog to digital converter(s) (ADC), digital to analog converter(s) (DAC), radio(s) (e.g., transmit and/or receive radio), antenna(s), buffer(s), or the like) configured to receive one or more signal(s) from the item(s) coupled thereto and perform one or more operations in response to the received signal.

The items of FIG. 2 do not include suffix reference designators so as to generally refer to the item. Thus, for example, the pump 112 refers to one or more of the pumps 112. The operations performed by the processing circuitry 256 may performed so as to automate one or more operations of the system 100.

The items illustrated as being communicatively coupled to the processing circuitry 256 include a valve 126, a sensor 108, a pump 112, a sensor 122, a dryer 124, an adapter 120, a camera 128, a sanitization activation device 132, a decontamination activation device 130, ventilation 146, and an ultraviolet source 148.

Some operations which the processing circuitry 256 may perform are now described with the understanding that this description is not exhaustive. The processing circuitry 256 can open, close, or change a position of a valve 126 or adapter 120 in response to one or more signals received from the sensor 122 and/or level sensor 108. The processing circuitry 256 can stop, start, or change a displacement rate of the pump 112 in response to one or more signals received from the sensor 122 and/or sensor 108. The processing circuitry 256 may activate or deactivate the ventilation 146, the dryer 124, the ultraviolet source 148, and/or the camera 128 in response to one or more signals from the sensor 122 and/or sensor 108.

The operations of the processing circuitry 256 may include one or more of the following operations:

1) The processing circuitry 256 may decrease a flow of liquid allowed through the valve 126 by at least partially closing the valve 126, such as in response to receiving a signal from the sensor 108 indicating the tank 142 and/or 144 is empty.

2) The processing circuitry 256 may increase a flow of liquid allowed through the valve 126 by at least partially closing the valve 126, such as in response to receiving a signal from the sanitization activation device 132 indicating that the sanitization activation device 132 was activated, the decontamination activation device 130 indicating that the decontamination device 130 was activated, an image from the camera 128 includes a user situated sufficiently near the outlet 104, and/or one or more signals from the sensor 122 (e.g., a proximity, motion, other sensor, or the like) indicating that a user is situated sufficiently near the outlet 104.

3) The processing circuitry 256 may stop or start the pump 112 in response to receiving one or more signals from the sanitization activation device 132 was activated, the decontamination activation device 130 indicating that the decontamination device 130 was activated, an image from the camera 128 includes a user situated sufficiently near the outlet 104, and/or one or more signals from the sensor 122 (e.g., a proximity, motion, other sensor, or the like) indicating that a user is situated sufficiently near the outlet 104.

4) The processing circuitry 256 may stop the pump 112 in response to a timer of the processing circuitry 256 indicating that a specified amount of time has elapsed since the pump 112 was activated.

5) The processing circuitry 256 may increase or decrease a flow of liquid allowed through the 2WV 126 and/or provided by the pump 112 in response to a sensor 122 indicating a pH of the fluid at the outlet 104 is too high (too basic) or too low (too acidic). The pH may be increased by adding anolyte and/or reducing catholyte. The pH may be decreased by adding catholyte and/or reducing anolyte.

6) The processing circuitry 256 may alter a fluid path of the adapter 120 in response to receiving a signal from the sanitization activation device 132 indicating that the sanitization activation device 132 was activated, the decontamination activation device 130 indicating that the decontamination device 130 was activated, an image from the camera 128 includes a user situated sufficiently near the outlet 104, one or more signals from the sensor 122 (e.g., a proximity, motion, other sensor, or the like) indicating that a user is situated sufficiently near the outlet 104, and/or one or more signals from a timer of the processing circuitry 256 indicating that a specified time of decontamination and/or sanitization has elapsed.

7) The processing circuitry 256 may activate the dryer 124 in response to a timer of the processing circuitry 256 indicating that a specified time of decontamination and/or sanitization has elapsed.

8) The processing circuitry 256 may deactivate the dryer 124 in response to a timer of the processing circuitry 256 indicating that a specified drying time has elapsed.

9) The processing circuitry 256 may activate the ventilation 146 and/or ultraviolet source 148 in response to one or more signals from the sanitization activation device 132 indicating that the sanitization activation device 132 was activated, the decontamination activation device 130 indicating that the decontamination device 130 was activated, an image from the camera 128 includes a user situated sufficiently near the outlet 104, one or more signals from the sensor 122 (e.g., a proximity, motion, other sensor, or the like) indicating that a user is situated sufficiently near the outlet 104.

10) The processing circuitry 256 may deactivate the ventilation 146 and/or ultraviolet source 148 in response to one or more signals from a timer of the processing circuitry 256 indicating that a specified decontamination time and/or sanitization time has elapsed, and/or from the sensor 122 or camera 128 indicating that the user is no longer sufficiently near the outlet 104.

11) The processing circuitry 256 may increase or decreasing a flow of liquid allowed through the 2WV 126 and/or provided by the pump 112 in response to a sensor 122 indicating FAC of the fluid at the outlet 104 is too high (indicating the fluid is too basic) or too low (indicating the fluid is too acidic). The FAC may be increased by adding anolyte and/or reducing catholyte. The FAC may be decreased by adding catholyte and/or reducing anolyte.

12) The processing circuitry 256 may stop the pump 112 in response to receiving a signal from the sensor 122 (e.g., a motion, proximity, biometric, face recognition, other sensor, or the like) indicating the user is no longer sufficiently proximate the outlet 104.

13) The processing circuitry 256 may record in a memory (see FIG. 4) video, audio, or other data that may indicate a time at which decontamination began and/or ended, a time at which sanitization began and/or ended, a time at which an intermittent drying between decontamination and sanitization began and/or ended, a user identification associated with the decontamination, sanitization, and/or drying, and/or a duration of the decontamination, sanitization, and/or drying.

14) The processing circuitry 256 may receive, through a user interface provided by the processing circuitry 256, an identification of a user or determining, such as through a biometric sensor (e.g., the sensor 122) a recognition of a face in an image provided by the camera, or the like.

15) The processing circuitry 256 may activate the UV source 148 in response to detecting the dryer 124 is activated, such as in embodiments in which the UV source 148 is part of or sufficiently proximate the dryer 124 (which may be implemented using a towel in one or more embodiments).

In embodiments in which the water inlet 102 includes individual hot and cold water lines, the anolyte and/or catholyte may be dosed into both the hot and cold water lines.

Figure 3:
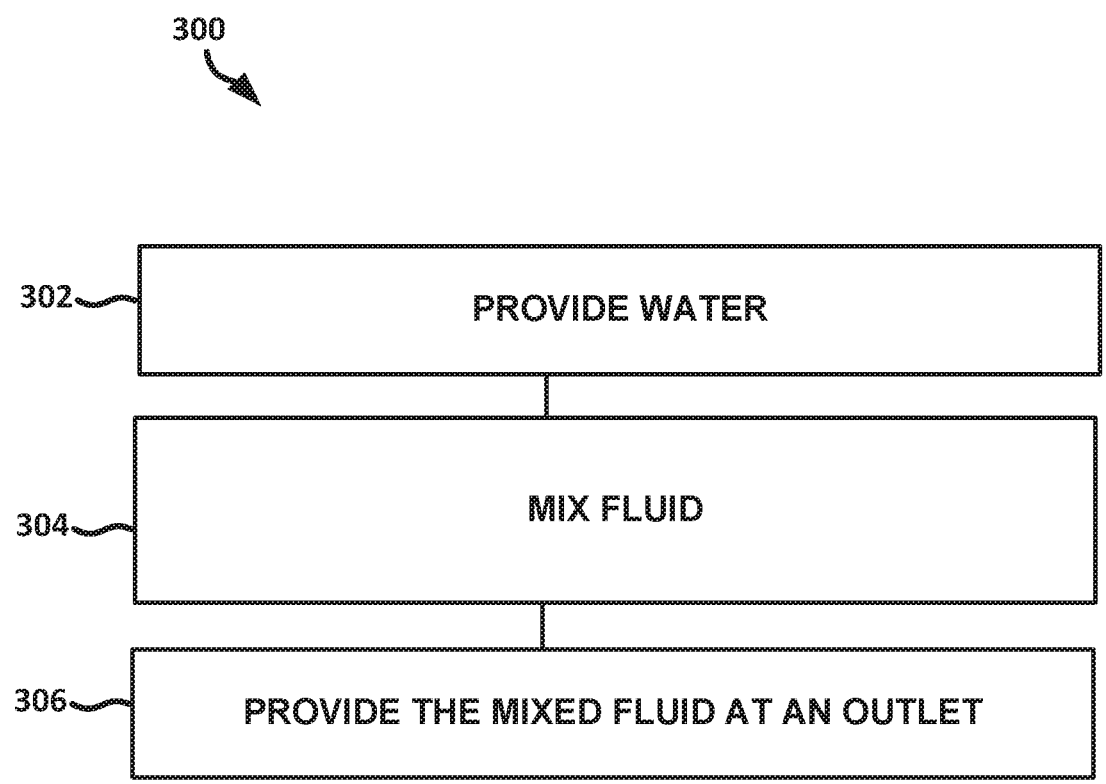
FIG. 3 illustrates, by way of example, a diagram of an embodiment of a method for decontamination and/or sanitization.

FIG. 3 illustrates, by way of example, a diagram of an embodiment of a method 300 for sanitization and/or decontamination, such as may be implemented using one or more of the components of the system 100. The method 300 as illustrated includes providing water, at operation 302; mixing fluids, at operation 304; and providing the mixed fluids at an outlet, at operation 306. The water may be provided by the water inlet 102. The operation 304 may be performed by the adapter 120. The operation 304 may include mixing two or more of (1) catholyte from the catholyte tank 142, (2) water from the water inlet 102, and (3) anolyte from the anolyte tank 144. The outlet 104 may be coupled to the adapter 120. The adapter 120 may be coupled between (1) the water inlet 102 and the outlet 104, (2) the catholyte tank 142 and the outlet 104, and/or (3) the anolyte tank 144 and the outlet 104.

The method 300 may further include providing, by the catholyte tank 142 or anolyte tank 144, catholyte or anolyte, respectively, to the adapter 120, such as by using a Venturi conduit and/or gravity. The method 300 may further include controlling a flow of catholyte from the catholyte tank 142 using a valve 126A coupled between the catholyte tank 142 and the adapter 120. The method 300 may further include controlling a flow of anolyte from the anolyte tank 144 using a valve 126B coupled between the anolyte tank 144 and the adapter 120.

The method 300 may further include controlling a flow of catholyte from the catholyte tank 142 using first pump 112A coupled between the catholyte tank 142 and the adapter 120. The method 300 may further include controlling a flow of anolyte from the anolyte tank 144 using a second pump 112B coupled between the anolyte tank 144 and the adapter 120. The method 300 may further include preventing fluid from flowing from the adapter 120 to the water inlet 102 using a valve 116C coupled between the water inlet 102 and the adapter 120. The method 300 may further include monitoring a pH or FAC and/or providing data indicative of one or more of a pH and/or an FAC of the fluid using a sensor 122 in fluid communication with the fluid.

The method 300 may further include increasing or decreasing a displacement rate of the pump 112A-B based on the data from the sensor 122 using processing circuitry 256 coupled to the sensor 122 and first and second pumps 112A-B. The method 300 may further include providing, using a first timer (of the processing circuitry 256), an indication in response to a specified amount of time elapsing since a beginning of a decontamination process in which catholyte is provided to the outlet 104. The method 300 may further include providing, using a second timer (of the processing circuitry 256), an indication in response to a specified amount of time elapsing since a beginning of a sanitization process in which anolyte is provided to the outlet 104. The method 300 may further include irradiating, using the ultraviolet source 148, a portion of the user between a decontamination process and a sanitization process.

The method 300 may further include activating the decontamination activation device 130 to indicate a beginning of the decontamination process. The method 300 may further include activating a sanitization activation device 132 to indicate a beginning of the sanitization process. The method 300 may further include determining, using a proximity, motion, bio-indicator, or optical sensor (e.g., the sensor 122), whether a user is near the outlet 104. The method 300 may further include initiating a decontamination or sanitization process in response to determining the user is near the outlet 104 based on data from the sensor 122.

The method 300 may further include determining when to initiate a decontamination process based on data provided by at least one of a sensor 122 and/or a timer (of the processing circuitry 256). The method 300 may further include determining when to terminate the decontamination process based on data provided by at least one of the sensor 122 and/or the timer (of the processing circuitry 256). The method 300 may further include determining when to initiate a drying process based on data provided by at least one of the sensor 122 and/or a timer (of the processing circuitry 256). The method 300 may further include determining when to terminate a drying process based on data provided by at least one of the sensor 122 and/or a timer (of the processing circuitry 256). The method 300 may further include determining when to initiate a sanitization process based on data provided by at least one of the sensor 122 and/or the timer (of the processing circuitry 256). The method 300 may further include determining when to terminate the sanitization process based on data provided by at least one of the sensor 122 and the timer (of the processing circuitry 256). The method 300 may further include determining whether to increase or decrease a displacement rate of a pump 112A-B coupled to the anolyte tank 144 or catholyte tank 142 based on data from a pH sensor or free available chlorine sensor (e.g., the sensor 122). The method 300 may further include stopping a pump 112B coupled to the anolyte tank 144 in response to determining a sanitization process is to be terminated. The method 300 may further include stopping a pump 112A coupled to the catholyte tank 142 in response to determining a decontamination process is to be terminated. The method 300 may further include closing a valve 126A coupled between the catholyte tank 142 and the adapter 120 in response to determining a decontamination process is to be terminated. The method 300 may further include closing a valve 126B coupled between the anolyte tank 144 and the adapter 120 in response to determining a sanitization process is to be terminated. The method 300 may further include opening a valve 126A coupled between the catholyte tank 142 and the adapter 120 in response to determining a decontamination process is to be initiated. The method 300 may further include opening a valve 126B coupled between the anolyte tank 144 and the adapter 120 in response to determining a sanitization process is to be initiated.

Figure 4:
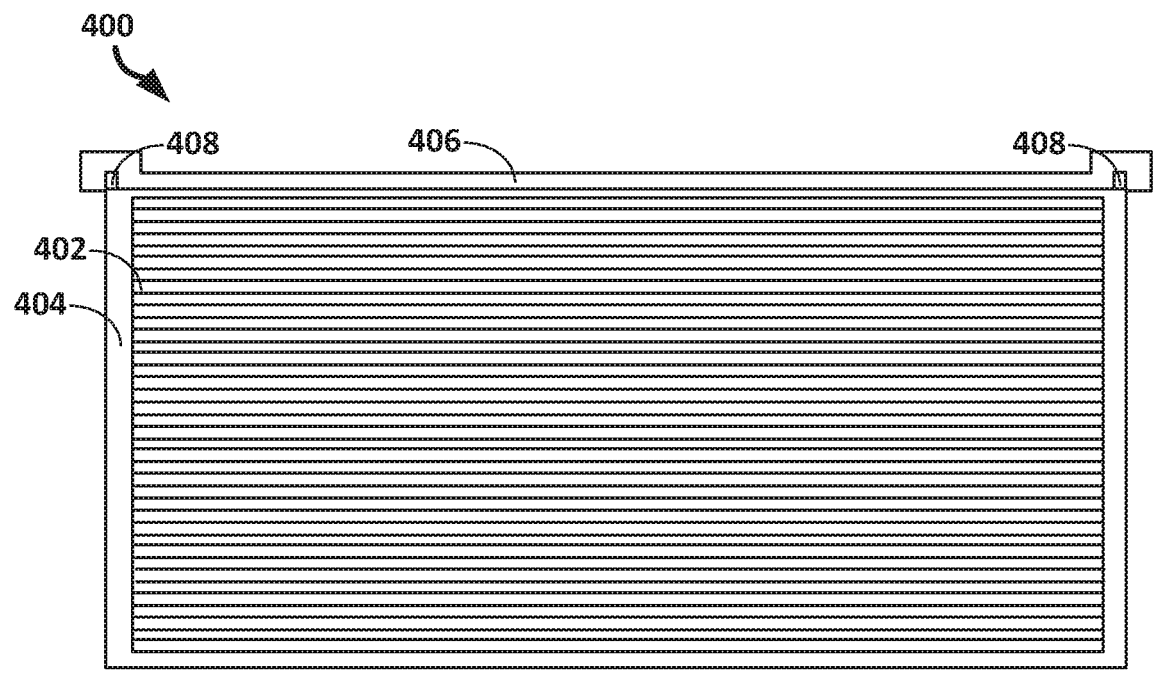
FIG. 4 illustrates, by way of example, a diagram of an embodiment of a container for cleaning and/or sanitization.

FIG. 4 illustrates, by way of example, a cross-section diagram of an embodiment of a container 400 that includes implements that can be used for cleaning and/or sanitization. The container 400 as illustrated includes a main body portion 404, a cover 406, an optional attachment mechanism 408, and fluid soaked fabric 402A situated within the main body portion 404. The container 400 can help keep the implements (e.g., the fabric 402) free from external contamination, yet allow for easy dispensing, and/or keep the fabric from drying out. The container 400 can be hermetic, or otherwise reduce an external environment influence on the fabric 402. The container 400 can be rigid, semi-rigid, flexible, stretchable, and/or the like. The container 400 can be a pouch, box, or other form of a container.

The fabric 402 can include a material, such as a non-woven fabric. The fabric 402 can include fibers of silk, cotton, polyester, wool, rayon, plastic resin, such as polyester, polyethylene, and polypropylene, other material, a combination thereof, or other material. The material of the fabric 402 can be absorbent, pliable, optionally stretchable, or the like. The fabric 402 can be soaked in, saturated by, or otherwise include a fluid, such as a diluted sanitizing or diluted cleansing agent. The sanitizing agent can include anolyte. The cleansing agent can include catholyte. The catholyte can be diluted 9:1 (water:catholyte) or otherwise diluted to a specified pH, such as a pH in a range from about 9.5-10.5. Anolyte can be diluted to a specified range in water or other fluid, such as about fifty to about five hundred parts per million free available chlorine, or the like. In one or more embodiments, the fabric 402 can include towels, towelettes, pads, brush (e.g., a nail brush or other brush), or other medium through which the sanitization or cleansing fluid can be provided to a user.

The body portion 404 can be closed by an optional mating cover 406. The body portion 404 can be made of plastic, metal, ceramic, resin, thermo-molded plastic, or the like. The body portion 404 can be produced using injection molding, forms, or the like. The body portion 404 can help prevent the liquid from evaporating from the fabric 402A.

The cover 406 can be used to help keep contamination away from the fabric 402. The cover 406 can include a same or different material as the body portion 404. The cover 406 can be flexible, rigid, semi-rigid, or the like. The cover 406 can be integrally formed with the body portion 404 or a discrete item. The cover 406 provides a mechanism that, when properly moved, can allow access to the fabric 402. The cover 406 provides a mechanism that, when properly situated on the body portion 404 and/or in contact with the attachment mechanism 408, helps keep contaminant or other external effects away from the fabric 402.

The attachment mechanism 408 can include an adhesive, a protrusion, a tab, a hole, a male or female connection portion, or the like. The attachment mechanism 408, when in contact with the cover 406, can provide a hermetic seal or otherwise keep external contaminants away from the fabric 402A.

Figure 5:
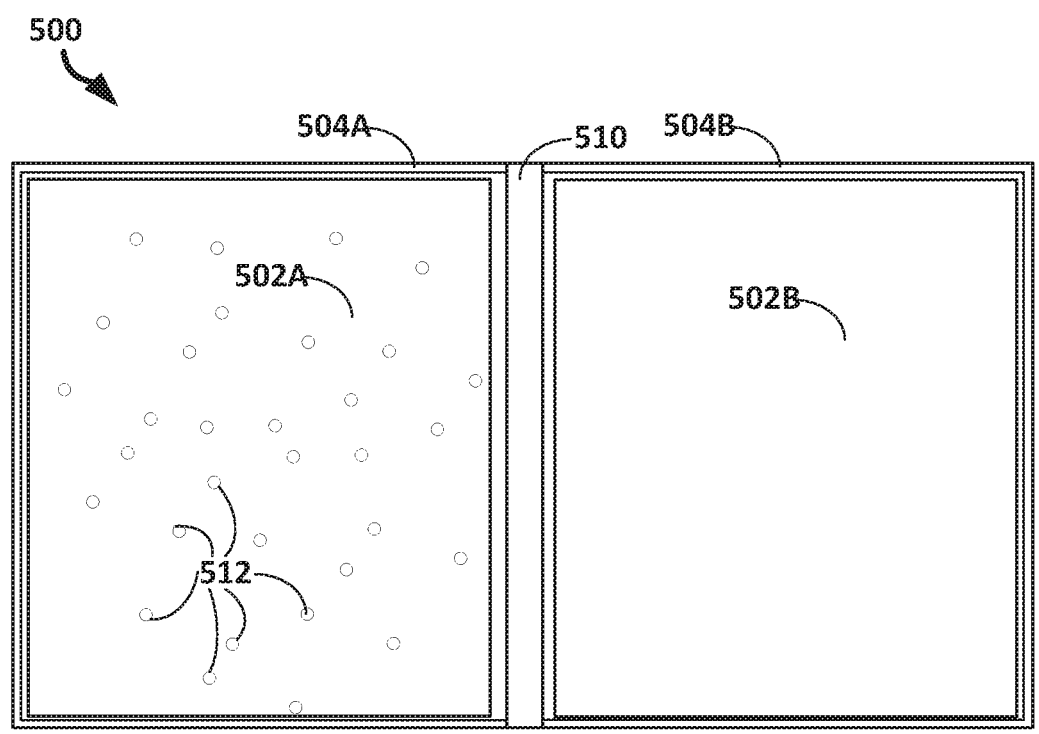
FIG. 5 illustrates, by way of example, a diagram of an embodiment of another container for cleaning and/or sanitization.

FIG. 5 illustrates, by way of example, a top view of a container 500. The container 500 can include a cover (not shown so as to not obscure the view of liquid-soaked fabrics 502A and 502B in the container 500). The container 500 can be similar to the container 400, with the container 500 including two body portions 504A and 504B that include respective fabrics 502A and 502B therein. The two body portions 404 are separated by a divider 510.

The divider 510 can be formed integral with the body portion 504A and/or 504B, attached to the body portion 504A and/or 504B, or discrete from the body portion 504A and/or 504B. The divider 510 can be made of a same or different material as the body portion 504A and/or 504B and/or the cover (not shown). The divider 510 can help keep fluid from the fabric 502A from contaminating the fabric 502B.

The fabrics 502A and 502B can be any type of the fluid-soaked fabrics 402 discussed above. For example, the fabric 502A can be a fabric that includes an anolyte such as a diluted anolyte and the fabric 402B can be a fabric that includes a catholyte such as a diluted catholyte. The fabrics 502A and 502B can be made of same or different materials, such as those discussed previously.

The fabric 502A as illustrated includes a friction-increasing material 512 thereon. While the fabric 502A is illustrated as including the friction-increasing material 512, both or neither of the fabrics 502A and 502B may include the friction-increasing material 512 thereon. In one or more embodiments, the fabrics 502A and 502B include the same or different friction-increasing materials thereon. The friction-increasing material 512 can include baking soda or other particles of a similar size that will not fully dissolve in the fluid in which the fabrics 502A and 502B are soaked. The friction-increasing material 512 can add grit to the fabric 502A, such as to add particulate friction to a surface or other object to which the fabric 502A is being applied. Such friction can aid in cleaning and/or sanitization.

A cover for the container 500 can include two separate covers, one for each body portion 504, a single cover that covers both body portions 504, or the like. The cover can be sealed against the body portions 504A and/or 504B and/or the divider 510, such as to help prevent cross-contamination between the body portions 504 and/or external contamination from contacting the fabrics 502A-502B.

The fabric(s) 402A-402B can be used with portions of or in lieu of portions of the system 100. The fabric(s) 402A-402B can provide a convenient, mobile way of providing non-toxic cleaning and/or sanitization.

The friction-increasing material 512, beyond its use on the fabrics 402, 502A, and 502B, can be used with the system 100. The friction-increasing material 512 can be introduced through the water inlet 102, the catholyte tank 142, anolyte tank 144, or provided independently to hands of the user, such as through the outlet 104 or through a different receptacle.

Figure 6:
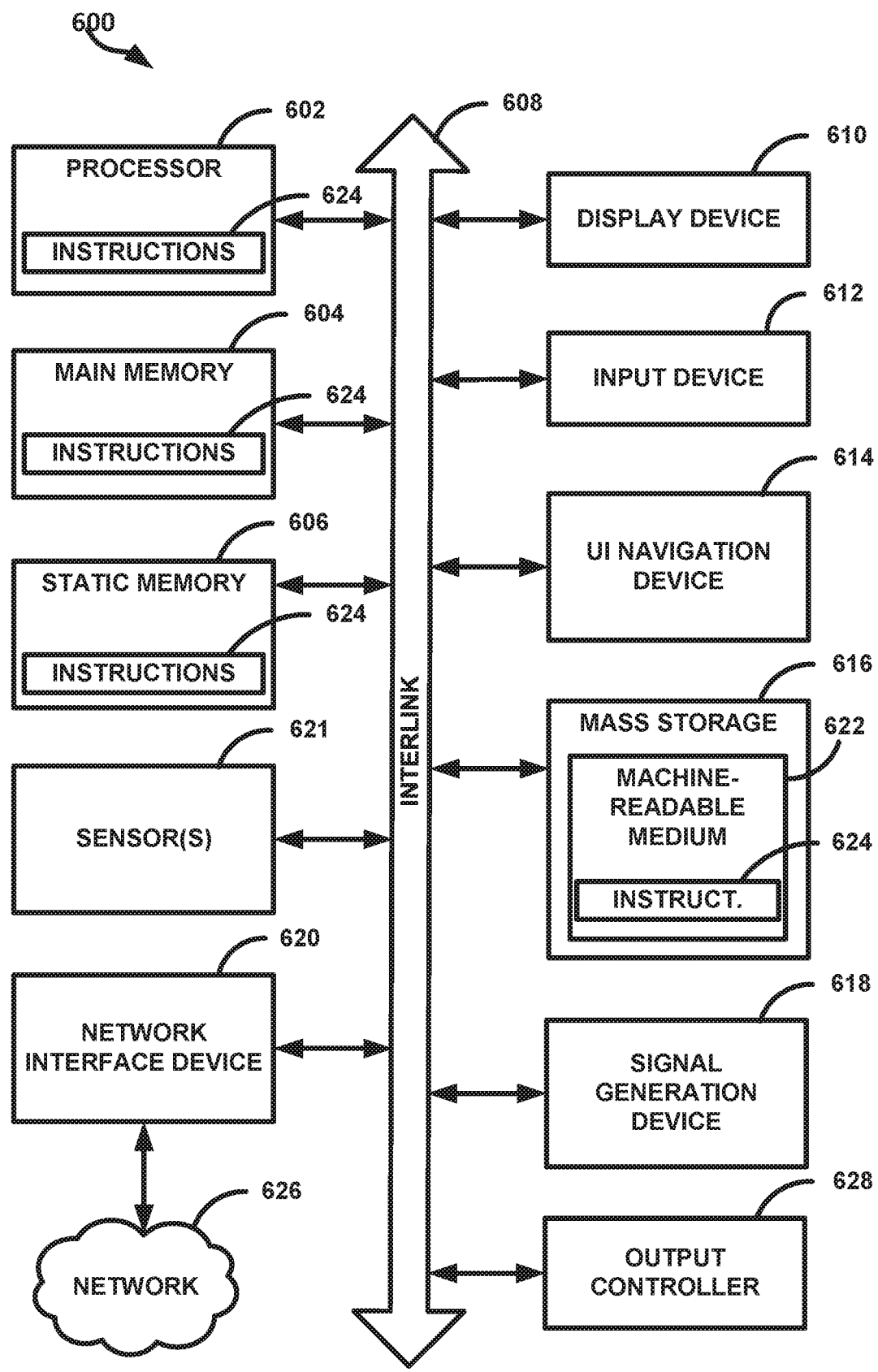
FIG. 6 illustrates, by way example, a diagram of an embodiment of a machine.

FIG. 6 illustrates, by way of example, a block diagram of an embodiment of a machine 600 on which one or more of the methods as discussed herein can be implemented. In one or more embodiments, one or more items of the processing circuitry 256 can be implemented by the machine 600. In alternative embodiments, the machine 600 operates as a standalone device or may be connected (e.g., networked) to other machines. In one or more embodiments, the processing circuitry 256 or other component of the system includes one or more of the items of the machine 600. In a networked deployment, the machine 600 may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example machine 600 includes a processor 602 (e.g., a central processing unit (CPU), a graphics processing unit (GPU) or both), a main memory 604 and a static memory 606, which communicate with each other via a bus 608. The machine 600 (e.g., computer system) may further include a video display unit 610 (e.g., a liquid crystal display (LCD) or a cathode ray tube (CRT)). The machine 600 also includes an alphanumeric input device 612 (e.g., a keyboard), a user interface (UI) navigation device 614 (e.g., a mouse), a disk drive unit 616, a signal generation device 618 (e.g., a speaker) and a network interface device 620.

The disk drive unit 616 includes a machine-readable medium 622 on which is stored one or more sets of instructions and data structures (e.g., software) 624 embodying or utilized by any one or more of the methodologies or functions described herein. The instructions 624 may also reside, completely or at least partially, within the main memory 604 and/or within the processor 602 during execution thereof by the machine 600, the main memory 604 and the processor 602 also constituting machine-readable media.

While the machine-readable medium 622 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and CD-ROM and DVD-ROM disks.

The instructions 624 may further be transmitted or received over a communications network 626 using a transmission medium. The instructions 624 may be transmitted using the network interface device 620 and any one of a number of well-known transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

EXAMPLES AND ADDITIONAL NOTES

Example 1 may include a system for decontamination and sanitization, the system comprising a water inlet to provide water to a first conduit, an outlet to provide a fluid to an end user, a catholyte tank to provide catholyte to a second conduit, an anolyte tank to provide anolyte to a third conduit, and an adapter coupled to the first, second, and third conduits, the adapter including one or more fluid paths therethrough to the outlet, the adapter to selectively provide one or more of the water, the catholyte, and the anolyte as the fluid.

In Example 2, Example 1 may include, wherein the conduit includes a Venturi conduit.

In Example 3, at least one of Examples 1-2 may further include, wherein the catholyte tank and the anolyte tank are situated so as to provide the catholyte and the anolyte, respectively, through gravity.

In Example 4, at least one of Examples 1-3 may further include a first two-way valve coupled between the catholyte tank and the adapter, and a second two-way valve coupled between the anolyte tank and the adapter.

In Example 5, Example 4 may further include a first pump coupled between the catholyte tank and the adapter to mobilize catholyte in the second conduit, and a second pump coupled between the anolyte tank and the adapter to mobilize anolyte in the third conduit.

In Example 6, Example 5 may further include a first check valve coupled between the water inlet and the adapter to help prevent flow of fluid from the adapter to the water inlet.

In Example 7, at least one of Examples 5-6 may further include a sensor in fluid communication with the fluid to monitor and provide data indicative of one or more of a pH and a free available chlorine (FAC) of the fluid.

In Example 8, Example 7 may further include processing circuitry coupled to the sensor and first and second pumps to increase or decrease a displacement rate of the pump based on the data from the sensor.

In Example 9, at least one of Examples 1-8 may further include a first timer to provide an indication in response to a specified amount of time elapsing since a beginning of a decontamination process in which catholyte is provided to the outlet.

In Example 10, Example 9 may further include a second time to provide an indication in response to a specified amount of time elapsing since a beginning of a sanitization process in which anolyte is provided to the outlet.

In Example 11, at least one of Examples 1-10 may further include an ultraviolet source to irradiate a portion of the user between a decontamination process and a sanitization process.

In Example 12, Example 11 may further include a dryer to remove liquid from the portion of the user between the decontamination process and the sanitization process.

In Example 13, Example 12 may further include, wherein the ultraviolet source is integral with the dryer.

In Example 14, at least one of Examples 9-13 may further include a decontamination activation device, wherein the beginning of the decontamination process is indicated by the decontamination activation device being activated by the user.

In Example 15, at least one of Examples 9-14 may further include a sanitization activation device, wherein the beginning of the sanitization process is indicated by the sanitization activation device being activated by the user.

In Example 16, at least one of Examples 1-15 may further include a proximity, motion, bio-indicator, or optical sensor to determine whether a user is near the outlet, and processing circuitry to initiate a decontamination or sanitization process in response to determining the user is near the outlet based on data from the sensor.

In Example 17, at least one of Examples 1-16 may further include processing circuitry to determine when to initiate a decontamination process based on data provided by at least one of a sensor and a timer, determine when to terminate the decontamination process based on data provided by at least one of the sensor and the timer, determine when to initiate a drying process based on data provided by at least one of the sensor and a timer, determine when to terminate a drying process based on data provided by at least one of the sensor and a timer, determine when to initiate a sanitization process based on data provided by at least one of the sensor and the timer, determine when to terminate the sanitization process based on data provided by at least one of the sensor and the timer, determine whether to increase or decrease a displacement rate of a pump coupled to the anolyte tank or catholyte tank based on data from a pH sensor or free available chlorine sensor, stop a pump coupled to the anolyte tank in response to determining a sanitization process is to be terminated, stop a pump coupled to the catholyte tank in response to determining a decontamination process is to be terminated, close a 2WV coupled between the catholyte tank and the adapter in response to determining a decontamination process is to be terminated, close a 2WV coupled between the anolyte tank and the adapter in response to determining a sanitization process is to be terminated, open a 2WV coupled between the catholyte tank and the adapter in response to determining a decontamination process is to be initiated, or open a 2WV coupled between the anolyte tank and the adapter in response to determining a sanitization process is to be initiated.

Example 18 may include a method of decontamination or sanitization comprising providing, by a water inlet, water, mixing fluids, at an adapter coupled to a catholyte tank, an anolyte tank, and the water inlet, one or more of (1) catholyte from a catholyte tank, (2) the provided water from the water inlet, and (3) anolyte from an anolyte tank, and providing, by an outlet coupled to the adapter, the mixed fluid.

In Example 19, Example 18 may further include providing, by the catholyte tank or anolyte tank, catholyte or anolyte, respectively, to the adapter.

In Example 20, Example 19 may further include, wherein providing the catholyte or anolyte includes using a Venturi conduit.

In Example 21, at least one of Examples 19-20 may further include, wherein providing the catholyte or anolyte includes using gravity.

In Example 22, at least one of Examples 18-21 may further include controlling a flow of catholyte from the catholyte tank using a first two-way valve coupled between the catholyte tank and the adapter, and controlling a flow of anolyte from the anolyte tank using a second two-way valve coupled between the anolyte tank and the adapter.

In Example 23, Example 22 may further include controlling a flow of catholyte from the catholyte tank using first pump coupled between the catholyte tank and the adapter, and controlling a flow of anolyte from the anolyte tank using a second pump coupled between the anolyte tank and the adapter.

In Example 24, Example 23 may further include preventing fluid from flowing from the adapter to the water inlet using a first check valve coupled between the water inlet and the adapter.

In Example 25, at least one of Examples 23-24 may further include monitoring and providing data indicative of one or more of a pH and a free available chlorine (FAC) of the fluid using a sensor in fluid communication with the fluid.

In Example 26, Example 25 may further include increasing or decreasing a displacement rate of the pump based on the data from the sensor using processing circuitry coupled to the sensor and first and second pumps.

In Example 27, at least one of Examples 18-26 may further include providing, using a first timer, an indication in response to a specified amount of time elapsing since a beginning of a decontamination process in which catholyte is provided to the outlet.

In Example 28, Example 27 may further include providing, using a second timer, an indication in response to a specified amount of time elapsing since a beginning of a sanitization process in which anolyte is provided to the outlet.

In Example 29, at least one of Examples 18-28 may further include irradiating, using an ultraviolet source, a portion of the user between a decontamination process and a sanitization process.

In Example 30, Example 29 may further include activating a decontamination activation device to indicate a beginning of the decontamination process.

In Example 31, Example 30 may further include activating a sanitization activation device to indicate a beginning of the sanitization process.

In Example 32, at least one of Examples 18-31 may further include determining, using a proximity, motion, bio-indicator, or optical sensor, whether a user is near the outlet, and initiating a decontamination or sanitization process in response to determining the user is near the outlet based on data from the sensor.

In Example 33, at least one of Examples 18-32 may further include determining when to initiate a decontamination process based on data provided by at least one of a sensor and a timer, determining when to terminate the decontamination process based on data provided by at least one of the sensor and the timer, determining when to initiate a drying process based on data provided by at least one of the sensor and a timer, determining when to terminate a drying process based on data provided by at least one of the sensor and a timer, determining when to initiate a sanitization process based on data provided by at least one of the sensor and the timer, determining when to terminate the sanitization process based on data provided by at least one of the sensor and the timer, determining whether to increase or decrease a displacement rate of a pump coupled to the anolyte tank or catholyte tank based on data from a pH sensor or free available chlorine sensor, stopping a pump coupled to the anolyte tank in response to determining a sanitization process is to be terminated, stopping a pump coupled to the catholyte tank in response to determining a decontamination process is to be terminated, closing a 2WV coupled between the catholyte tank and the adapter in response to determining a decontamination process is to be terminated, closing a 2WV coupled between the anolyte tank and the adapter in response to determining a sanitization process is to be terminated, opening a 2WV coupled between the catholyte tank and the adapter in response to determining a decontamination process is to be initiated, or opening a 2WV coupled between the anolyte tank and the adapter in response to determining a sanitization process is to be initiated.

Example 34 includes a non-transitory machine-readable medium including instructions that, when executed by a device, cause the device to perform the method of one or more of examples 18-33.

Example 35 includes a system comprising a container and a first fabric including diluted catholyte in the container.

In Example 36, Example 35 can further include, wherein the container includes a first section and a second section, the first fabric in the first section, and the system further comprises a second fabric including diluted anolyte in the second section of the container.

In Example 37, Example 36 can further include a divider between the first and second sections, the divider helping prevent fluid communication between the first and second sections.

In Example 38, Example 37 can further include a cover to mate with container, such that when the cover is properly situated on the container, the cover prevents fluid from leaking out of the container.

In Example 39, Example 38 can further include, wherein the container includes a flexible pouch.

In Example 40, Example 38 can further include, wherein the container includes a rigid plastic material.

In Example 41, at least one of Examples 38-40 can further include, wherein at least one of the first and second fabrics includes a friction-increasing material thereon.

In Example 42, Example 41 can further include, wherein the friction-increasing material includes baking soda.

In Example 43, at least one of Examples 36-42 can further include, wherein the first and second fabrics include towelettes or pads.

In Example 44, Example 43 further includes, wherein first and second fabrics comprise a non-woven material.

Example 45 includes a device consistent with the disclosure.

Example 46 includes a system consistent with the disclosure.

Although an embodiment has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

What is claimed is:

1. A method of decontamination or sanitization comprising:
providing, by a water inlet, water;
mixing fluids, at an adapter coupled to a catholyte tank, an anolyte tank, and the water inlet, including two or more of (1) catholyte from a catholyte tank, (2) the provided water from the water inlet, and (3) anolyte from an anolyte tank;
providing, by an outlet coupled to the adapter, the mixed fluid; and irradiating, by an ultraviolet source, a portion of a user between a decontamination process and a sanitization process.

2. The method of claim 1, further comprising providing, by the catholyte tank or anolyte tank, catholyte or anolyte, respectively, to the adapter.

3. The method of claim 2, wherein providing the catholyte or anolyte includes using a Venturi conduit.

4. The method of claim 2, wherein the catholyte tank and the anolyte tank are situated so as to provide the catholyte and the anolyte, respectively, through gravity.

5. The method of claim 2, wherein the catholyte is provided to the adapter through a first two-way valve coupled between the catholyte tank and the adapter; and the anolyte is provided through a second two-way valve coupled between the anolyte tank and the adapter.

6. The method of claim 5, further comprising mobilizing, by a first pump coupled between the catholyte tank and the adapter, the catholyte to the adapter.

7. The method of claim 6, further comprising, mobilizing, by a second pump coupled between the anolyte tank and the adapter, the anolyte to the adapter.

8. The method of claim 5, further comprising preventing, by a first check valve coupled between the water inlet and the adapter, flow of the mixed fluids from the adapter to the water inlet.

9. The method of claim 7, further comprising providing, by a sensor in fluid communication with the fluid, data indicative of one or more of a pH and a free available chlorine (FAC) of the fluid.

10. The method of claim 9, further comprising increasing or decreasing, by processing circuitry coupled to the sensor and first and second pumps, a displacement rate of the first or second pump based on the data from the sensor.

11. The method of claim 1, further comprising providing, by a first timer, an indication in response to a specified amount of time elapsing since a beginning of a decontamination process in which catholyte is provided to the outlet.

12. The method of claim 11, further comprising providing, by a second timer, an indication in response to a specified amount of time elapsing since a beginning of a sanitization process in which anolyte is provided to the outlet.

13. The method of claim 1, further comprising removing, by a dryer, liquid from the portion of the user between the decontamination process and the sanitization process.

14. The method of claim 13, wherein the ultraviolet source is integral with the dryer.

15. The method of claim 10, further comprising indicating, by a decontamination activation device activated by the user, a beginning of the decontamination process.

16. The method of claim 12, further comprising indicating, by a sanitization activation device, a beginning of the sanitization process being activated by the user.

17. The method of claim 1, further comprising determining, by a proximity, motion, bio-indicator, or optical sensor, whether a user is near the outlet.

18. The method of claim 17, further comprising initiating, by processing circuitry, a decontamination or sanitization process in response to determining the user is near the outlet based on data from the sensor.

19. The method of claim 1, further comprising:
determining when to initiate a decontamination process, by processing circuitry, based on data provided by at least one of a sensor and a timer;
determining, by the processing circuitry, when to terminate the decontamination process based on data provided by the at least one of the sensor and the timer;
determining, by the processing circuitry, when to initiate a drying process based on data provided by the at least one of the sensor and the timer;
determining, by the processing circuitry, when to terminate a drying process based on data provided by the at least one of the sensor and the tinier;
determining, by the processing circuitry, when to initiate a sanitization process based on data provided by the at least one of the sensor and the timer;
determining, h the processing circuitry, when to terminate the sanitization process based on data provided by the at least one of the sensor and the timer;
determining, by the processing circuitry, whether to increase or decrease a displacement rate of a pump coupled to the anolyte tank or catholyte tank based on data from a pH sensor or free available chlorine sensor;
stopping, by the processing circuitry, a pump coupled to the anolyte tank in response to determining a sanitization process is to be terminated;
stopping, by the processing circuitry, a pump coupled to the catholyte tank in response to determining a decontamination process is to be terminated;
closing, by the processing circuitry, a 2WV coupled between the catholyte tank and the adapter in response to determining a decontamination process is to be terminated;
closing, by the processing circuitry, a 2WV coupled between the anolyte tank and the adapter in response to determining a sanitization process is to be terminated;
opening, by the processing circuitry, a 2WV coupled between the catholyte tank and the adapter in response to determining a decontamination process is to be initiated; or
opening, by the processing circuitry, a 2WV coupled between the anolyte tank and the adapter in response to determining a sanitization process is to be initiated.

* * * * *

UNITED STATES PATENT AND TRADEMARK OFFICE
CERTIFICATE OF CORRECTION

PATENT NO. : 10,688,208 B2
APPLICATION NO. : 16/057146
DATED : June 23, 2020
INVENTOR(S) : Thomas Johnson Page 1 of 1

It is certified that error appears in the above-identified patent and that said Letters Patent is hereby corrected as shown below:

In the Claims

In Column 17, Line 48, in Claim 15, delete "claim 10," and insert --claim 11,-- therefor In Column 18, Line 21, in Claim 19, delete "tinier;" and insert --timer;-- therefor In Column 18, Line 25, in Claim 19, delete "h" and insert --by-- therefor Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*